US009557256B2

United States Patent
Seok et al.

(10) Patent No.: US 9,557,256 B2
(45) Date of Patent: Jan. 31, 2017

(54) TENSION AND COMPRESSION TESTER FOR FRACTURE STRESS TEST OF COMPACT PIPE SAMPLE

(71) Applicant: Research & Business Foundation SUNGKYUNKWAN UNIVERSITY, Suwon-si (KR)

(72) Inventors: Changsung Seok, Gwacheon-si (KR); Suk Woo Hong, Seoul (KR)

(73) Assignee: Research & Business Foundation SUNGKYUNKWAN UNIVERSITY, Suwon-si (KR)

( * ) Notice: Subject to any disclaimer, the term of this patent is extended or adjusted under 35 U.S.C. 154(b) by 77 days.

(21) Appl. No.: 14/755,563

(22) Filed: Jun. 30, 2015

(65) Prior Publication Data
US 2016/0003721 A1   Jan. 7, 2016

(30) Foreign Application Priority Data
Jul. 1, 2014   (KR) ........................ 10-2014-0081973

(51) Int. Cl.
*G01N 3/08*   (2006.01)
*G01N 3/02*   (2006.01)
*G01N 3/04*   (2006.01)

(52) U.S. Cl.
CPC ...... *G01N 3/08* (2013.01); *G01N 3/02* (2013.01); *G01N 3/04* (2013.01);
(Continued)

(58) Field of Classification Search
CPC .......... G02N 3/08; G01B 5/30; G01M 99/008; G01N 13/00; G01N 2203/0066; G01N 2203/0067; G01N 2203/0435
(Continued)

(56) References Cited

U.S. PATENT DOCUMENTS

| 5,602,329 A * | 2/1997 | Haubensak | G01N 3/08 73/105 |
| 2010/0281963 A1* | 11/2010 | Greer | G01N 3/08 73/82 |

(Continued)

FOREIGN PATENT DOCUMENTS

KR   10-1132002 B1   3/2012

OTHER PUBLICATIONS

Seok, Changsung, "Destructive Resistance Test for Leak before Break Design." KSME Journal (2011) 12., vol. 51, No. 12: p. 37-41 (14 pages with English translation).
(Continued)

*Primary Examiner* — Lisa Caputo
*Assistant Examiner* — Nigel Plumb
(74) *Attorney, Agent, or Firm* — NSIP Law

(57) ABSTRACT

A tension and compression tester for a fracture stress test of a compact pipe sample having a crack portion formed thereon, comprises: a pair of holders each of which is configured to surround both ends of the compact pipe sample respectively such that the crack portion is interposed between both ends of the compact pipe; fixing portions each of which is disposed between the compact pipe sample and the holder to enhance fastening between the compact pipe sample and the holder; levers each of which is connected with the fixing portion and the holder to deliver tension or bending to the compact pipe sample; and separation preventing portions for fixing both ends of the holder and the lever with each other to prevent separation of the lever and the holder. Accordingly, the tester can conduct both tension and compression tests, while easily applying loads on the sample during the test.

12 Claims, 7 Drawing Sheets

(52) U.S. Cl.
CPC ............... *G01N 2203/0066* (2013.01); *G01N 2203/0274* (2013.01); *G01N 2203/0435* (2013.01)

(58) Field of Classification Search
USPC .......................... 73/821, 818, 788, 760, 790
See application file for complete search history.

(56) References Cited

U.S. PATENT DOCUMENTS

2013/0006542 A1* 1/2013 Matsubara ............... G01N 3/34
702/34
2013/0192383 A1* 8/2013 Reed ........................ G01N 3/08
73/818

OTHER PUBLICATIONS

Korean Office Action issued on Jan. 14, 2015 in counterpart Korean Application No. 10-2014-0081973. (5 pages).

* cited by examiner

TENSION AND COMPRESSION TESTER FOR FRACTURE STRESS TEST OF COMPACT PIPE SAMPLE

CROSS-REFERENCE TO RELATED APPLICATIONS

This application claims priority from Korean Patent Application No. 10-2014-0081973, filed on Jul. 1, 2014 in the Korean Intellectual Property Office, the disclosure of which is incorporated herein by reference in its entirety.

BACKGROUND

1. Field

Embodiments of the present disclosure relate to a tension and compression tester for a fracture stress test of a compact pipe sample, and more specifically, to a tension and compression tester for a fracture stress test of a compact pipe, which is capable of conducting both tension and compression tests while applying loads on the sample with ease through a lever during the fracture stress test of the compact pipe sample.

2. Description of Related Art

It is necessary to obtain the fracture stress of pipe system structure to apply Leak Before Break (LBB) design concept on the pipe system structure such as a nuclear power plant which can generate considerable problems in the society once emergency occurs.

However, it is practically difficult to conduct a full-scale test, considering that it takes numerous pipes and testers to conduct tests, and subsequently requires increased costs and time to obtain the fracture stress of the pipe system structure.

It has been thus suggested to obtain the fracture stress of a material using standard sample tests and evaluate the fracture stress of the pipe system structure based on the obtained fracture stress, rather than testing with numerous pipes and tests.

That is, the American Society for Testing and Materials (ASTM) suggested the Compact Tension (CT) or Single Edge Notched Bending (SENB) sample as a standard sample.

While the standard samples like those mentioned above can provide advantage of standardized sample shapes and testing methods, there is also a limit in the manufacture of the sample due to pipe curvatures and thicknesses.

Further, to obtain the fracture stress, it is necessary to consider the constraint effects from the geometric shapes or dimensions of the sample, and the influence of the constraint effect is greater on the structure like piping. It is accordingly necessary to adjust the constraint effect even when the test is conducted with the standard sample.

Meanwhile, a miniature pipe sample has been devised using portions taken from the real pipes, based on the pipe curvature, thickness, etc. to eliminate need for adjustment of constraint effect influence which is generated due to changes in the size and shape of the sample. However, the sample and the lever deformed during loading, which in turn caused variations in the test results. Further, spacing between the lever and holder or sample caused insufficient loading during loading process.

Further, the existent fracture stress tester for a pipe sample is disadvantageous because it is designed in consideration of loading either in the tension direction or in the compression direction only, and thus can conduct only one type of test. Accordingly, a tester is necessary, which can deliver all of the tension, compression, and bending received from the loader and the lever to the pipe sample during the pipe fracture stress test.

SUMMARY

Exemplary embodiments of the present inventive concept overcome the above disadvantages and other disadvantages not described above. Also, the present inventive concept is not required to overcome the disadvantages described above, and an exemplary embodiment of the present inventive concept may not overcome any of the problems described above.

According to an embodiment, a technical objective is to provide a tension and compression tester for a fracture stress test of a compact pipe sample, which is capable of performing both tension and compression tests, while applying loads on the sample with ease through a lever during the fracture stress test of the compact pipe sample.

It is another technical objective to provide a tension and compression tester for a fracture stress test of a compact pipe sample, which is capable of preventing deformation and breakage of the compact pipe sample and the lever during the fracture stress test of the compact pipe sample.

According to an embodiment, a tension and compression tester for a fracture stress test of a compact pipe sample having a crack portion formed thereon may comprises: a pair of holders each of which is configured to surround both ends of the compact pipe sample respectively such that the crack portion is interposed between the both ends of the compact pipe; fixing portions each of which is disposed between the compact pipe sample and the holder to enhance fastening between the compact pipe sample and the holder; levers each of which is connected with the fixing portion and the holder to deliver tension or bending to the compact pipe sample; and separation preventing portions for fixing both ends of the holder and the lever with each other to prevent separation of the lever and the holder.

Each of the separation preventing portions may comprises: a first separation preventing portion for preventing separation of the lever and one end of the holder when the tension is applied on the compact pipe sample; and a second separation preventing portion for preventing separation of the lever and the other end of the holder when the compression is applied on the compact pipe sample.

The first separation preventing portion and the second separation preventing portion may comprise: a frame having a through hole into which the holder and the lever are inserted; and an insert disposed between the frame and the lever.

The compact pipe sample includes a groove on an end, the groove being depressed inward, and the fixing portion may comprise a ring member mounted on the groove, and a locking member disposed between the ring member and the holder to prevent separation of the ring member.

The holder may have threads on the inner wall, and the locking member may have threads formed on an outer surface thereof corresponding to the threads of the holder.

The tension and compression tester for a fracture stress test of a compact pipe sample may further comprise an insert member inserted into the compact pipe to correspond to a location of the holder and to support loads applied on the compact pipe sample.

According to embodiments, one single tension and compression tester for the fracture stress test of the compact pipe sample is provided, which can conduct both tension and compression tests of the compact pipe sample.

Further, loads can be delivered without loss to the sample during application of loads on the compact pipe sample, since separation of the holders surrounding both ends of the compact pipe sample and the levers for delivering the loads to the holders is prevented.

Further, the sample escaping from the holders during application of loads can be prevented, since fastening with the holders is reinforced by the insertion of rings into grooves formed on the compact pipe sample.

Further, during application of loads, generation of a crack on an area other than an intended crack portion of the compact pipe sample can be prevented using insert members.

BRIEF DESCRIPTION OF THE DRAWINGS

The above and/or other aspects of the present inventive concept will be more apparent by describing certain exemplary embodiments of the present inventive concept with reference to the accompanying drawings, in which.

DETAILED DESCRIPTION

Certain exemplary embodiments of the present inventive concept will now be described in greater detail with reference to the accompanying drawings.

An embodiment of the present disclosure relates to a tension and compression tester for a fracture stress test of a compact pipe, which is capable of conducting both tension and compression tests while applying loads on the sample with ease through a lever during fracture stress test of the compact pipe sample.

Figure 1:
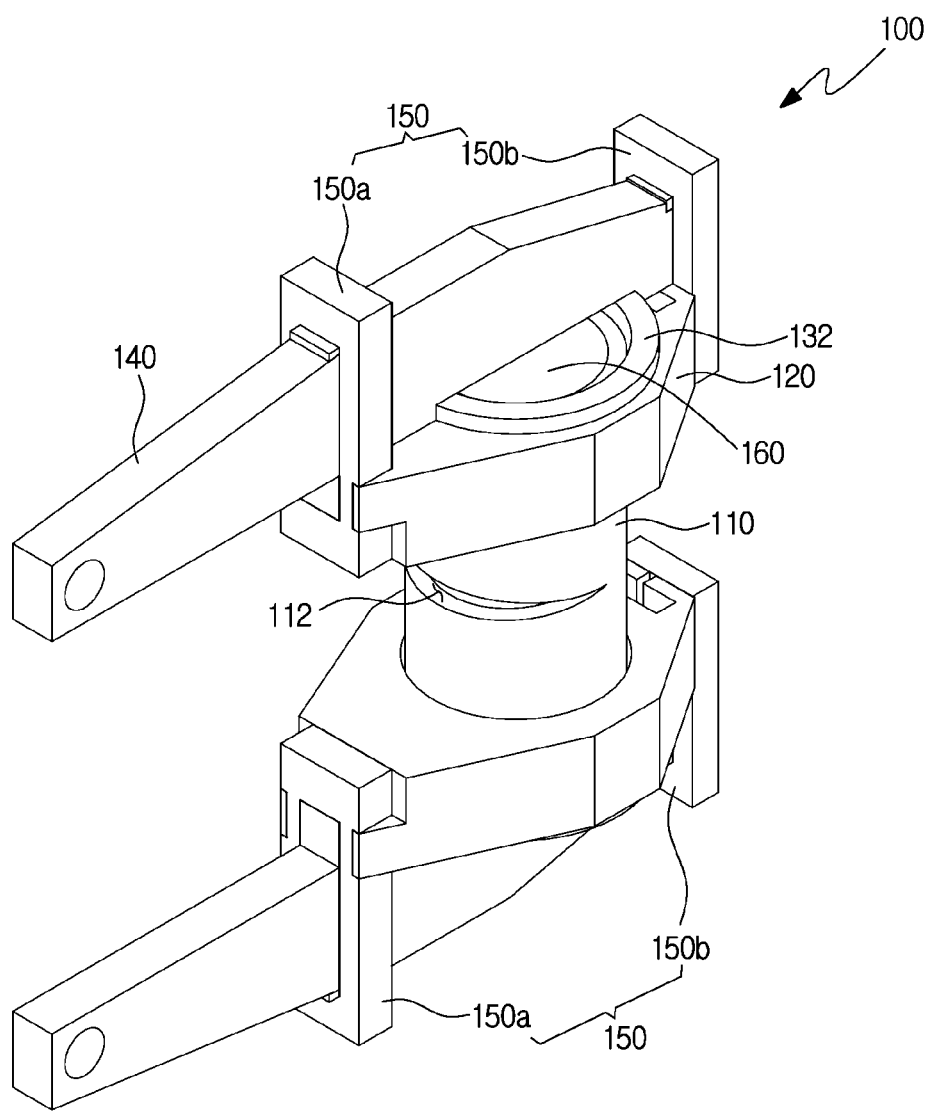
FIG. 1 is a schematic perspective view of a tension and compression tester for a fracture stress test of a compact pipe sample according to an embodiment of the present disclosure.
Figure 2:
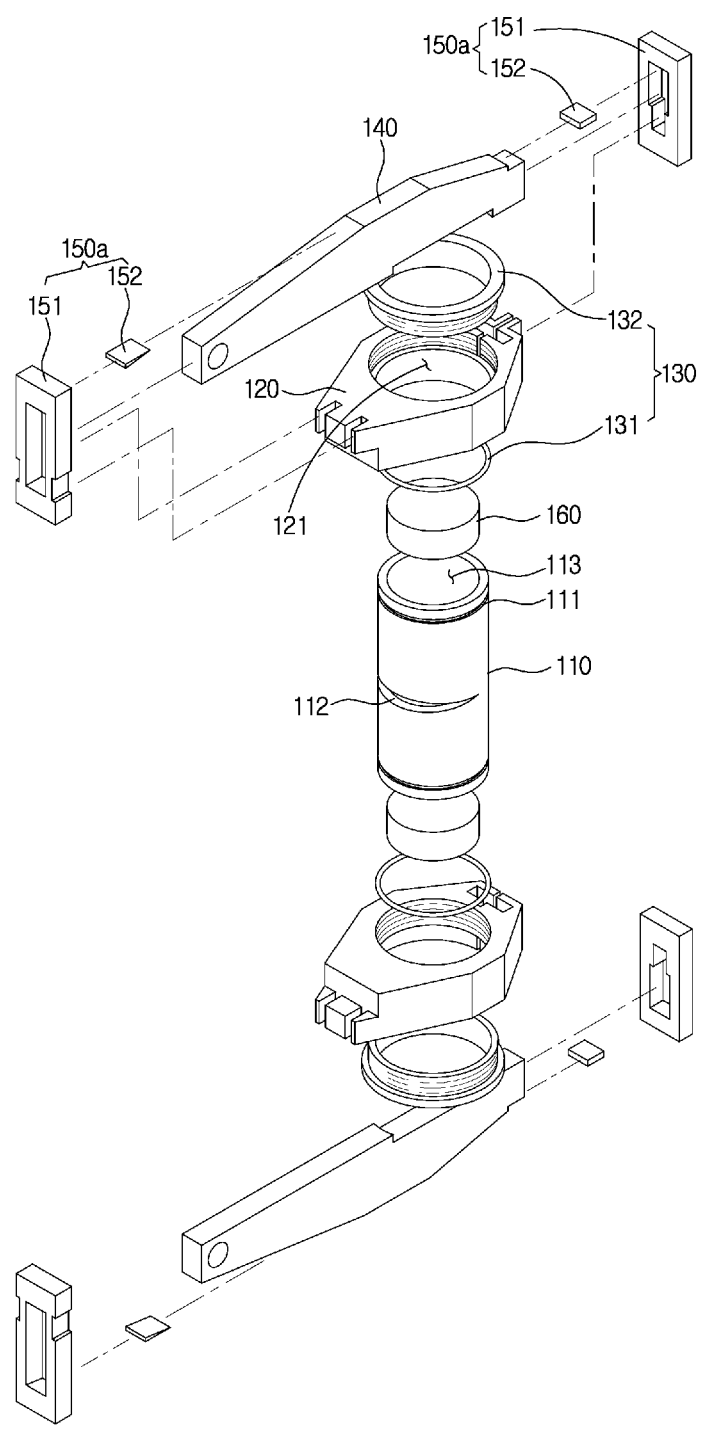
FIG. 2 is a schematic, exploded perspective view of the tension and compression tester for a fracture stress test of a compact pipe sample of FIG. 1.

FIG. 1 is a schematic perspective view of a tension and compression tester for a fracture stress test of a compact pipe sample according to an embodiment of the present disclosure, and FIG. 2 is a schematic, exploded perspective view of the tension and compression tester for a fracture stress test of a compact pipe sample of FIG. 1. Referring to FIGS. 1 and 2, the tension and compression tester 100 for a fracture stress test of a compact pipe sample includes a compact pipe sample 110, holders 120 surrounding both ends of the compact pipe sample 110, fixing portions 130 interposed between the compact pipe sample 110 and the holders 120, levers 140 coupled with the fixing portions 130 and the holders 120, separation preventing portions 150 coupling the levers 140 with the holders 120, and insert members 160 inserted in the compact pipe sample 110.

The compact pipe sample 110 is the subject to be fixed by the holders 120, and it is provided from a real-scale pipe. The compact pipe sample 110 includes grooves 111 depressed inward on the ends of the compact pipe sample to be fastened with ring members 131. According to an embodiment, the grooves 111 may be formed on both ends of the compact pipe sample 110, but the present disclosure is not limited thereto. Accordingly, the groove 111 may be formed on only one end, although it is preferable that the grooves 111 are formed on both ends to increase fastening between the compact pipe sample 110 and the holders 120.

The compact pipe sample 110 has a crack portion 112 in the middle where the crack occurs in the fracture resistance testing. Further, the compact pipe sample 110 has a hollow portion 113 which is in connection with outside along a direction of center axis. The crack is formed only at a location of the crack portion 113 by the insertion of the insert members 160 into the hollow portion 113. That is, it is possible to prevent inadvertent occurrence of cracks at an area where an operator does not intend during loading on the compact pipe sample 110, and by forming the crack portion 113 at an intended area, the operator can also predict an area where the crack would occur.

The holders 120, or, a pair of holders 120 are disposed on both ends of the compact pipe sample 110, surrounding both ends of the compact pipe sample 110 with through holes 121, and distributing loads so that the loads are evenly delivered to both ends of the compact pipe sample 110 surrounded by the holders 120. The holders 120 may preferably extend in a lengthwise direction, to allow easy insertion into through holes of the separation preventing portions 150.

The holders 120 have the through holes 121 passing through both upper and lower surfaces, and the upper portion of the compact pipe sample 110 is inserted into the through holes 121. The upper end of the compact pipe sample 110 is inserted to be protruded at least above the plane where the upper surface of the holder 120 is formed, and preferably is inserted until the upper end of the compact pipe sample 110 and the upper surface of the holder 120 are aligned on the same plane.

The through holes 121 are preferably formed in a greater diameter than the diameter of the compact pipe sample 110. By doing so, it is possible to arrange the compact pipe sample 110, the ring members 131, locking members 132 and the holders in sequence, with increased fastening between the holders 120 and the compact pipe sample 110. The through holes 121 may have threads on walls thereof. When the threads are formed on the outer surface of the locking members 132 (to be explained), the threads of the locking members may allow the locking members 132 to move along the walls of the through holes 121 or fixed at a location in contact with the ring members 131.

The fixing portions 130 are disposed between the compact pipe sample 110 and the holders 120 to increase fastening between the compact pipe sample 110 and the holders 120. The fixing portions 130 include the ring members 131 and the locking members 132.

The ring members 131 are mounted on the grooves 111 of the compact pipe sample 110, respectively, to enhance fastening between the compact pipe sample 110 and the holders 120 by providing an effect as if the compact pipe sample 110 is force-fit in the holders 120. Specifically, it is ideal that the outer surface of the compact pipe sample 110 and the through holes 121 of the holders 120 correspond to each other, but since this is practically impossible, fastening between the compact pipe sample 110 and the holders 120 is deteriorated, resulting in the compact pipe sample 110 escaping from the holders 120. Accordingly, the ring members 130 are disposed between the outer surface of the compact pipe sample 110 and the through holes 121 of the holders 120 to prevent deterioration of fastening due to space between the outer surface of the compact pipe sample 110 and the through holes 121 of the holders 120.

The ring members 131 are preferably formed of an elastic material. That is, the diameter of the compact pipe sample 110 including the ring members 131 is greater than the diameter of the through holes 121 of the holders 120 including the locking members 132, to cause the ring members 131 to be compressed during fastening of the compact pipe sample 110 including the ring members 131 and the holders 120 including the locking members 132, and such compression provides a substantial force-fitting effect.

Meanwhile, respective parts of the ring members 130 may be divided along a circumferential direction to move away from each other or approach each other, so that the ring members 130 are mounted effectively on the grooves of the compact pipe sample 110.

The locking members 132 are configured between the ring members 131 and the holders 120 to enhance fastening between the holders 120 and the compact pipe sample 110, and thus prevent separation of the ring members 131 from the grooves 111. Specifically, when the compact pipe sample 110 is under loading, the loading applied on the compact pipe sample 110 can cause the ring members 131 to escape from the grooves 111, which in turn causes problems such as separation of the compact pipe sample 110 from the holders 120. This can be addressed by disposing the locking members 132 between the ring members 131 and the through holes 121 of the holders 120. Meanwhile, the locking members 132 may have threads on the outer surfaces opposite to an inner surface of the holders 120. The threads of the locking members may be formed corresponding to the through holders 120, and the locking members 132 can be moved along the through holes 121 or fixed at a specific location within the through holes 121.

Figure 3:
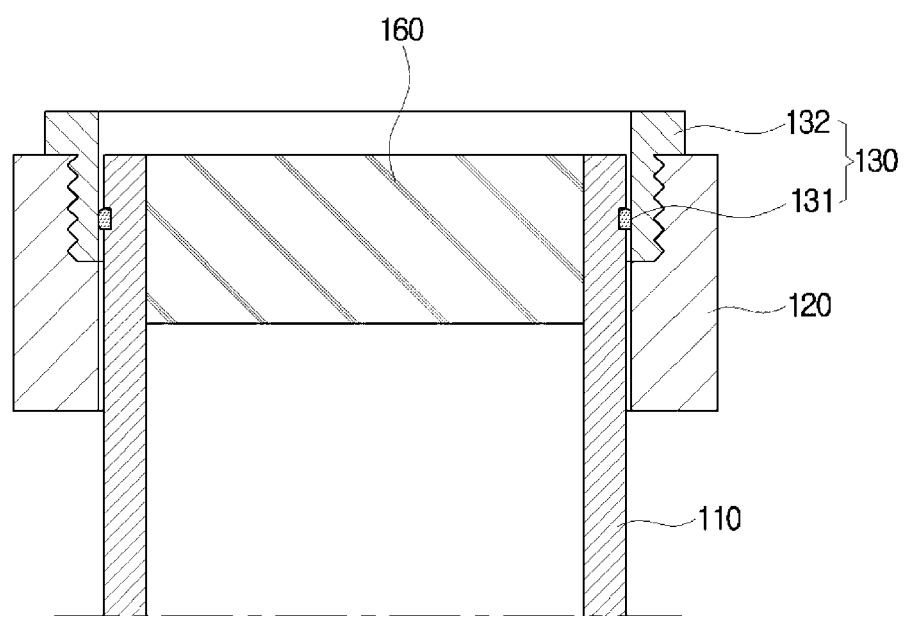
FIG. 3 is a schematic, cross sectional view illustrating the relationship between the sample and the holders fastened with each other in the tension and compression tester for a fracture stress test of a compact pipe sample of FIG. 1.
Figure 4:
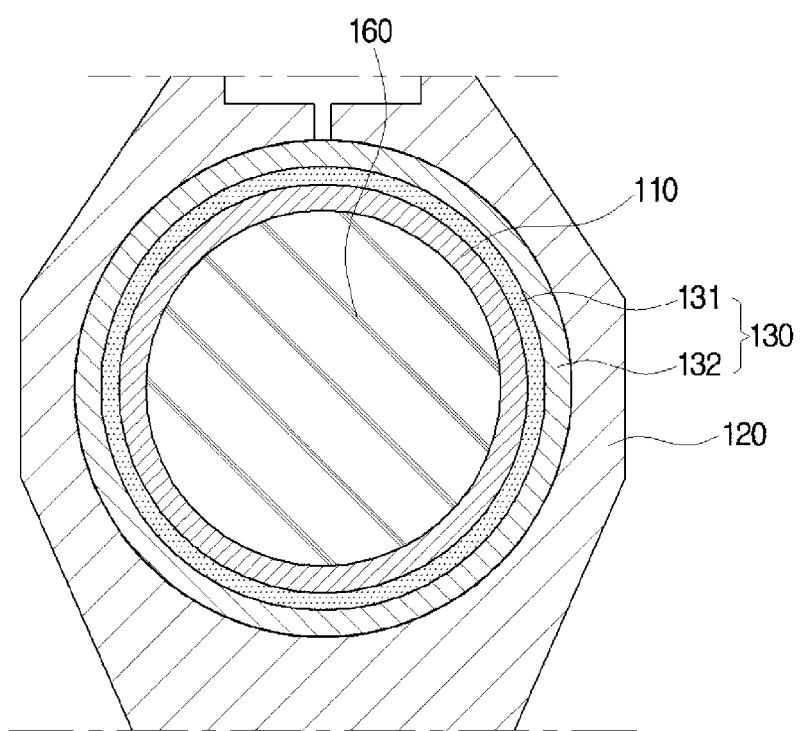
FIG. 4 is a schematic, top view illustrating the relationship between the sample and the holders fastened with each other in the tension and compression tester for a fracture stress test of a compact pipe sample of FIG. 1.

FIG. 3 is a schematic, cross sectional view illustrating the relationship between the sample and the holders fastened with each other in the tension and compression tester for a fracture stress test of a compact pipe sample of FIG. 1, and FIG. 4 is a schematic, top view illustrating the relationship between the sample and the holders fastened with each other in the tension and compression tester for a fracture stress test of a compact pipe sample of FIG. 1. To describe again the relationship between the compact pipe sample 110 and the holders 120 and the fixing portions 130, the ring members 131 and the locking members 132 are disposed between the compact pipe sample 110 and the through holes 121 of the holders 120. In other words, in a radial direction from the compact pipe sample 110, the ring members 131, the locking members 132, and the holders 120 are arranged in sequence. As shown in FIG. 4, compared to the spacing between the compact pipe sample 110 and the holders 120, the sum of the width of the ring members 131 and the width of the locking members 132 may be smaller. Moreover, the thickness of the locking members 132 preferably may be the same as or larger that the thickness of the ring members 131.

The levers 140 are configured to deliver the loads applied from the load applying portions L to the sample, and are connected with the holders 120 and the fixing portions 130.

The levers 140 prepared are longer than the length of the holders 120 so that the levers 140 are able to apply greater bending on the compact pipe sample 110 with less tension. The fastening between the holders 120 and the fixing portions 130 is enhanced by fastening the levers 140 with the holders 120 and the locking members 132 of the fixing portions 130.

The separation preventing portions 150 are configured to enable both tension and compression tests during the fracture stress test of the compact pipe sample 110, and to prevent separation of the levers 140 and the holders 120 from each other. The separation preventing portions 150 include first separation preventing portions 150a and second separation preventing portions 150b.

The first separation preventing portions 150a are configured to fasten one ends of the holders 120 with the levers 140, to thus prevent separation of the levers 140 and the holders 120 during tension test, and the second separation preventing portions 150b are configured to fasten the other ends of the holders 120 with the levers 140 to prevent separation of the levers 140 and the holders 120 during compression test. The first and second separation preventing portions 150a, 150b will be collectively explained below, as these have identical configuration and shape.

The separation preventing portions 150 include frames 151 and inserts 152. The frames 151 include through holes to receive ends of the holders 120 and the levers 140 inserted therein. The inserts 152 are configured to be inserted into the through holes of the frames 151 to minimize separation between the holders 120 and the levers 140 and the frames 151. If the thickness of the levers 140 and the holders 120 are different from the sizes of the through holes, despite the levers 140 and the holders 120 being inserted into the through holes, the levers 140 and the holders 120 can be separated from each other during tension or compression test, thus failing to properly apply the loads, and generating errors. By disposing the inserts 152 between the frames 151 and the levers 140, the levers 140 and the holders 120 are force-fit in the through holes, and the separation is prevented.

The inserting members 160 are mounted in the hollow portion 113 of the compact pipe sample 110 and positioned at locations opposite to the holders 120 to support the loads delivered to the compact pipe sample 110. It may be difficult for the compact pipe sample 110 to efficiently support the loads if the sample 110 has a thin thickness, and even if the compact pipe sample 110 has the crack portion 112 formed therein, the compact pipe sample 110 may develop cracks at other sites before the crack portion 112 develops crack, when the loads exceed considerably above the fracture that the compact pipe sample 110 can resist. Accordingly, the insert members 160 may be inserted in the hollow portion 113 of the compact pipe sample 110, or to be more specific, inserted into locations opposite to locations where the holders 120 are mounted. By doing so, it is possible to effectively support the loads delivered to the compact pipe sample 110 and make the crack occur at the crack portion 112.

The operation of a tension and compression tester for a fracture stress test of a compact pipe sample according to an embodiment will be explained below.

Figure 5:
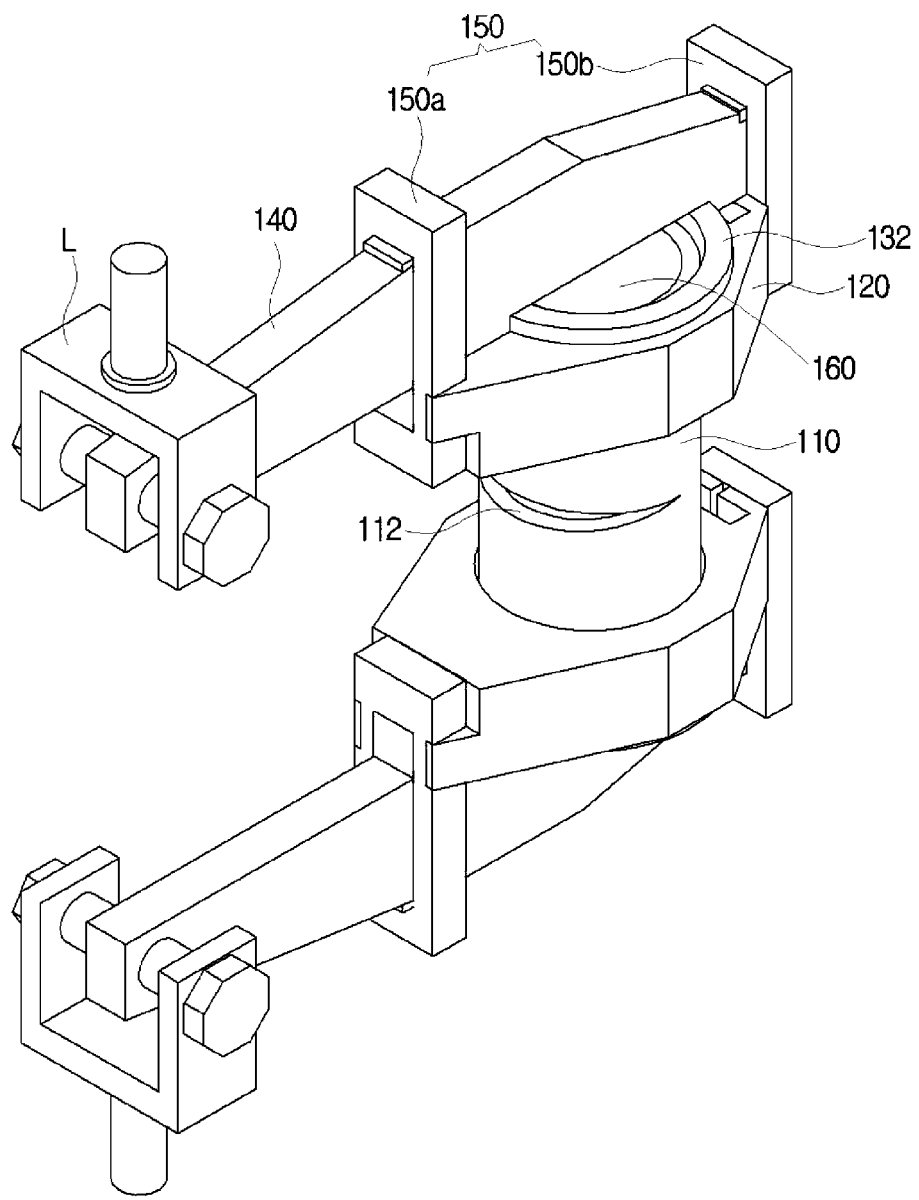
FIG. 5 illustrates the tension and compression tester for a fracture stress test of a compact pipe sample of FIG. 1 under loading.

FIG. 5 illustrates the tension and compression tester for a fracture stress test of a compact pipe sample of FIG. 1 under loading. Referring to FIG. 5, first, the compact pipe sample 110 is mounted in the through holes of the holders 120. At this time, the ring members 131 are mounted on the grooves 111 of the compact pipe sample 110, and the locking members 132 are mounted between the holders 120 and the ring members 131 to enhance the fastening between the holders 120 and the compact pipe sample 110. Next, the levers are firmly fastened to the fixing portions 130 and the holders 120, after which both ends of the holders 120 and the levers 140 are firmly fastened via the separation preventing portions 150.

When the fastening between the holders 120 and the compact pipe sample 110 is completed, the load applying portions L are fastened with the levers 140. The tension and compression testing is then conducted.

Figure 6:
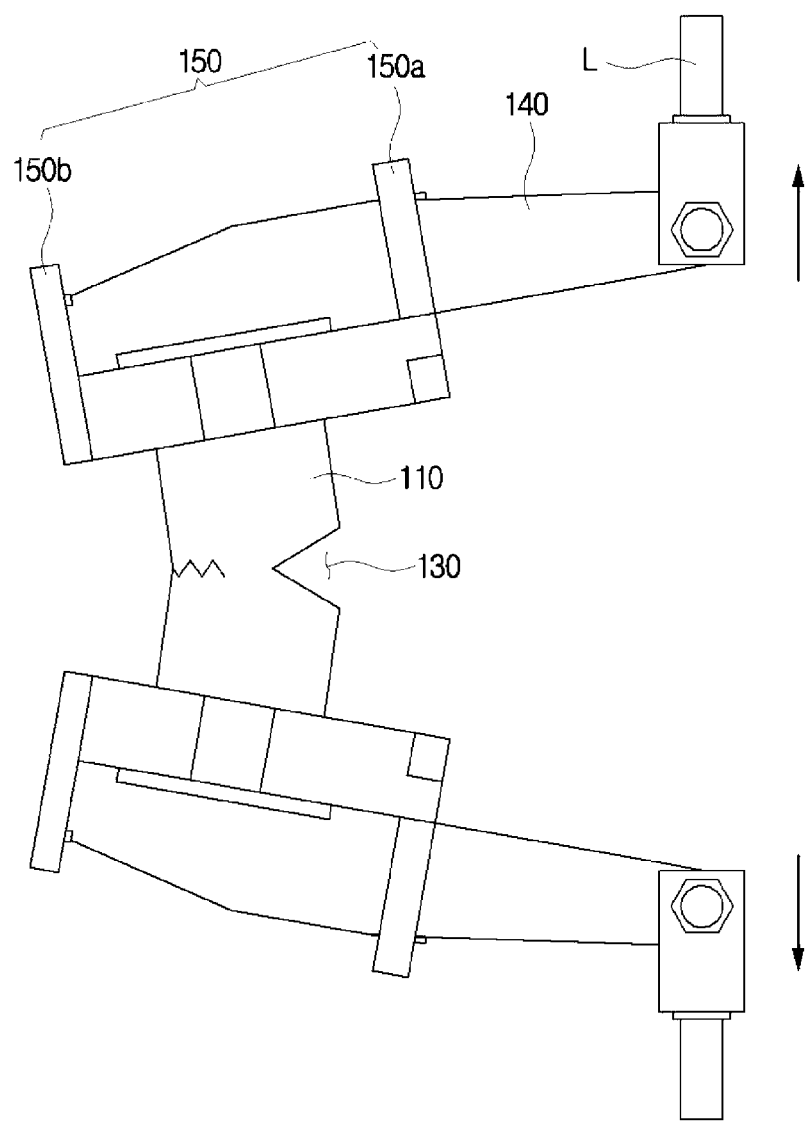
FIG. 6 schematically illustrates the tension and compression tester for a fracture stress test of a compact pipe sample of FIG. 1 in the tension testing state.

FIG. 6 schematically illustrates the tension and compression tester for a fracture stress test of a compact pipe sample of FIG. 1 in the tension testing state. Referring to FIG. 6, the load applying portions L connected to the levers 140 are moved in a direction away from each other. At this time, the first separation preventing portions 150a prevent separation of the levers 140 and the holders 120. As a result, tension is exerted on the compact pipe sample 110 without loss, and the tension test is conducted based on the crack occurring at the crack portion 112.

Figure 7:
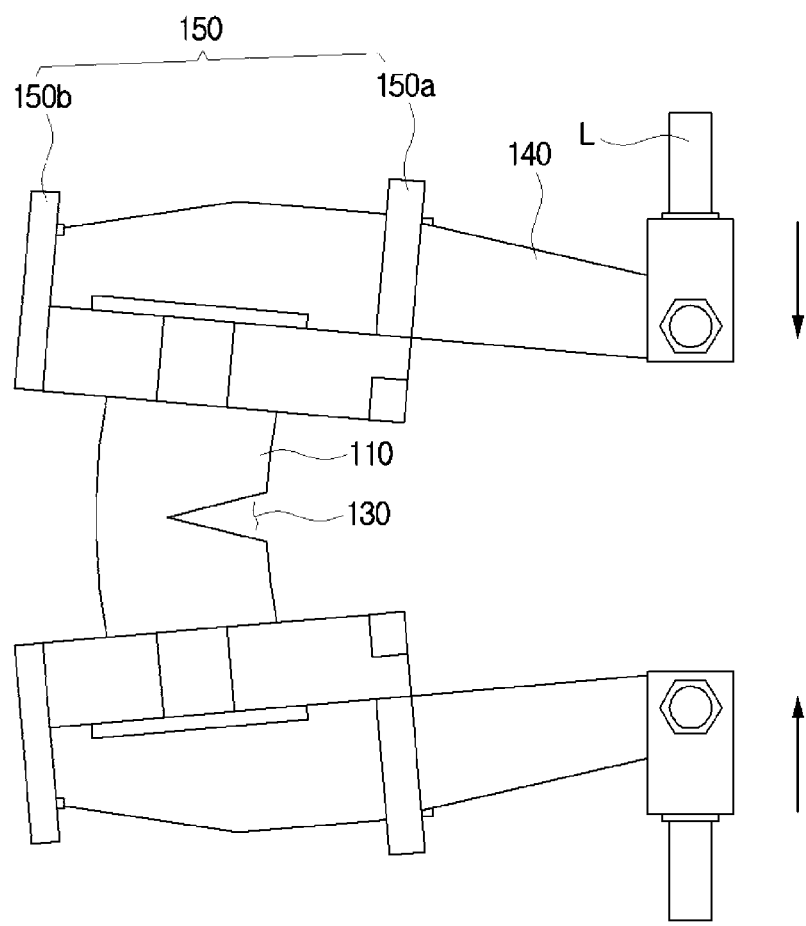
FIG. 7 schematically illustrates the tension and compression tester for a fracture stress test of a compact pipe sample of FIG. 1 in the compression testing state.

FIG. 7 schematically illustrates the tension and compression tester for a fracture stress test of a compact pipe sample of FIG. 1 in the compression testing state. Referring to FIG. 7, the load applying portions L connected to the levers 140 are moved in a direction closer to each other. At this time, the second separation preventing portions 150b prevent separation of the levers 140 and the holders 120. As a result, the compression is exerted on the compact pipe sample 110 without loss, and the compression test is conducted accordingly.

According to embodiments of the present disclosure, a tension and compression tester for a fracture stress test of a compact pipe sample is provided, which is capable of conducting both tension and compression tests, while applying loads on the sample with ease through the levers, during the fracture stress test of the compact pipe sample.

The foregoing exemplary embodiments and advantages are merely exemplary and are not to be construed as limiting the exemplary embodiments. The present teaching can be readily applied to other types of apparatuses. Also, the description of the exemplary embodiments of the present inventive concept is intended to be illustrative, and not to limit the scope of the claims.

DESCRIPTION OF THE REFERENCE NUMERALS

| | |
|---|---|
| 100: Tension and compression tester for a fracture stress test of a compact pipe sample | |
| 110: Compact pipe sample | 120: Holder |
| 130: Fixing portion | 140: Lever |
| 150: Separation preventing portion | 160: Insert member |

What is claimed is:

1. A tension and compression tester for a fracture stress test of a compact pipe sample having a crack portion formed thereon, comprising:
   a pair of holders each of which is configured to surround both ends of the compact pipe sample respectively such that the crack portion is interposed between the both ends of the compact pipe;
   fixing portions each of which is disposed between the compact pipe sample and the holder to enhance fastening between the compact pipe sample and the holder;
   levers each of which is connected with the fixing portion and the holder to deliver tension or bending to the compact pipe sample; and
   separation preventing portions for fixing both ends of the holder and the lever with each other to prevent separation of the lever and the holder.

2. The tension and compression tester for a fracture stress test of a compact pipe sample of claim 1, wherein each of the separation preventing portions comprises:
   a first separation preventing portion for preventing separation of the lever and one end of the holder when the tension is applied on the compact pipe sample; and
   a second separation preventing portion for preventing separation of the lever and the other end of the holder when the compression is applied on the compact pipe sample.

3. The tension and compression tester for a fracture stress test of a compact pipe sample of claim 2, wherein the first separation preventing portion and the second separation preventing portion comprise:
   a frame having a through hole into which the holder and the lever are inserted; and
   an insert disposed between the frame and the lever.

4. The tension and compression tester for a fracture stress test of a compact pipe sample of claim 3, wherein the compact pipe sample includes a groove on an end, the groove being depressed inward, and wherein the fixing portion comprises a ring member mounted on the groove, and a locking member disposed between the ring member and the holder to prevent separation of the ring member.

5. The tension and compression tester for a fracture stress test of a compact pipe sample of claim 4, wherein the holder has threads on the inner wall, and wherein the locking member has threads formed on an outer surface thereof corresponding to the threads of the holder.

6. The tension and compression tester for a fracture stress test of a compact pipe sample of claim 5, further comprising an insert member inserted into the compact pipe to correspond to a location of the holder and to support loads applied on the compact pipe sample.

7. The tension and compression tester for a fracture stress test of a compact pipe sample of claim 2, wherein the compact pipe sample includes a groove on an end, the groove being depressed inward, and wherein the fixing portion comprises a ring member mounted on the groove, and a locking member disposed between the ring member and the holder to prevent separation of the ring member.

8. The tension and compression tester for a fracture stress test of a compact pipe sample of claim 7, wherein the holder has threads on the inner wall, and wherein the locking member has threads formed on an outer surface thereof corresponding to the threads of the holder.

9. The tension and compression tester for a fracture stress test of a compact pipe sample of claim 8, further comprising an insert member inserted into the compact pipe to correspond to a location of the holder and to support loads applied on the compact pipe sample.

10. The tension and compression tester for a fracture stress test of a compact pipe sample of claim 1, wherein the compact pipe sample includes a groove on an end, the groove being depressed inward, and wherein the fixing portion comprises a ring member mounted on the groove, and a locking member disposed between the ring member and the holder to prevent separation of the ring member.

11. The tension and compression tester for a fracture stress test of a compact pipe sample of claim 10, wherein the holder has threads on the inner wall, and wherein the locking member has threads formed on an outer surface thereof corresponding to the threads of the holder.

12. The tension and compression tester for a fracture stress test of a compact pipe sample of claim 7, further comprising an insert member inserted into the compact pipe to correspond to a location of the holder and to support loads applied on the compact pipe sample.

\* \* \* \* \*